(12) United States Patent
Boraiah (10) Patent No.: US 7,824,419 B2
(45) Date of Patent: Nov. 2, 2010

(54) LAPAROSCOPIC TROCAR AND FACIAL CLOSURE SYSTEMS AND METHODS

(76) Inventor: Sreevathsa Boraiah, 300 E. 93$^{rd}$ St., Apt. C., New York, NY (US) 10128

( * ) Notice: Subject to any disclaimer, the term of this patent is extended or adjusted under 35 U.S.C. 154(b) by 265 days.

(21) Appl. No.: 11/673,280

(22) Filed: Feb. 9, 2007

(65) Prior Publication Data

US 2007/0213757 A1  Sep. 13, 2007

Related U.S. Application Data

(60) Provisional application No. 60/766,747, filed on Feb. 9, 2006.

(51) Int. Cl.
*A61B 17/04* (2006.01)
(52) U.S. Cl. .................. 606/144; 606/139; 606/148
(58) Field of Classification Search .............. 606/185, 606/186, 167, 144, 139, 148, 133, 145; 604/272, 604/264; 27/24.1; 112/169
See application file for complete search history.

(56) References Cited

U.S. PATENT DOCUMENTS

| | | | | |
|---|---|---|---|---|
| 5,320,632 A | * | 6/1994 | Heidmueller | 606/144 |
| 5,364,408 A | * | 11/1994 | Gordon | 606/144 |
| 5,372,588 A | * | 12/1994 | Farley et al. | 604/170.01 |
| 5,374,275 A | * | 12/1994 | Bradley et al. | 606/144 |
| 5,403,328 A | * | 4/1995 | Shallman | 606/144 |
| 5,470,338 A | * | 11/1995 | Whitfield et al. | 606/144 |
| 5,527,321 A | * | 6/1996 | Hinchliffe | 606/144 |
| 5,540,704 A | * | 7/1996 | Gordon et al. | 606/144 |
| 5,573,540 A | * | 11/1996 | Yoon | 606/139 |
| 5,575,800 A | * | 11/1996 | Gordon | 606/144 |
| 5,586,986 A | * | 12/1996 | Hinchliffe | 606/147 |
| 5,860,991 A | * | 1/1999 | Klein et al. | 606/144 |
| 6,743,241 B2 | * | 6/2004 | Kerr | 606/144 |
| 6,960,164 B2 | | 11/2005 | O'Heeron | |
| 2003/0105473 A1 | * | 6/2003 | Miller | 606/139 |
| 2003/0181924 A1 | * | 9/2003 | Yamamoto et al. | 606/144 |
| 2005/0149066 A1 | * | 7/2005 | Stafford | 606/144 |

* cited by examiner

*Primary Examiner*—Anhtuan T Nguyen
*Assistant Examiner*—David Eastwood
(74) *Attorney, Agent, or Firm*—John A. Artz; Dickinson Wright PLLC (57) ABSTRACT

A laparoscopic trocar and facial closure system. A trocar having a shaft member and a pointed tip, a telescoping cannular assembly having a pair of sleeve members, a needle receptor assembly having another sleeve member that is positioned over the shaft member, a needle actuation mechanism with a needle actuation rod having a handle, a needle assembly, and a needle release mechanism. Also, embodiments include a body member, a C-shaped portion, a pair of wings and a pivotal deployment mechanism for deploying the wings.

4 Claims, 6 Drawing Sheets

LAPAROSCOPIC TROCAR AND FACIAL CLOSURE SYSTEMS AND METHODS

CROSS-REFERENCE TO RELATED APPLICATION

The present invention claims priority from U.S. Provisional Application Ser. No. 60/766,747, entitled "LAPAROSCOPIC TROCAR AND FACIAL CLOSURE SYSTEMS AND METHODS", filed Feb. 9, 2006.

BACKGROUND

Endoscopic surgery is a significant method of performing surgical operations and has become the surgical procedure of choice due to its patient care advantages over "open surgery". A particular type of endoscopic surgery is laparoscopic surgery. A significant advantage of laparoscopic surgery over open surgery is the decreased post-operative recovery time. In most instances, a patient is able to leave the hospital within hours after laparoscopic surgery has been performed, whereas with open surgery, a patient requires several days of hospital care to recover. Additionally, laparoscopic surgery achieves decreased incidents of post-operative abdominal adhesions, decreased tissue damage, decreased post-operative pain, and enhanced cosmetic results. Laparoscopic surgery consequently permits the patient to return to normal activity in a short period of time.

Conventionally, a laparoscopic surgical procedure begins with the insufflation of the abdominal cavity with carbon dioxide. The introduction of this gas into the abdominal cavity lifts the abdominal wall away from the internal viscera. The abdominal wall is then pierced or penetrated with two or more devices known as trocars. A trocar includes a housing assembly, a piercing element referred to as an obturator, and a shaft that extends therebetween. A cannula assembly, having a cylindrical port element, is slid over the shaft. After insertion of the trocar through the abdominal wall of the patient, the obturator is removed by the surgeon while leaving the port element protruding through the abdominal wall. The port element may be fixed in place by using a fascia device, and laparoscopic surgical instruments can then be inserted through the port element to view internal organs and to perform surgical procedures.

Notwithstanding the advantages afforded by laparoscopic surgery, such technique has associated disadvantages. Specifically, the puncture wounds created within the body by the surgeon to gain access to the surgical site are often difficult and time-consuming to close, and can place great demands on the surgeon. Such tasks are made even more difficult when laparoscopic surgery is performed upon obese patients where there is a relatively deep puncture wound formed through a relatively small puncture site or incision. Indeed, the puncture site frequently needs to be enlarged following the laparoscopic procedure to ensure that the site is closed at the interior abdominal wall. In addition, many laparoscopic closure devices are incapable of deploying a suture a sufficient distance about the puncture site to fashion an appropriate closure. Such limited distance fails to sufficiently approximate the peritoneum and fascia surrounding the puncture site sufficiently to form an adequate closure.

One laparoscopic device is that described in U.S. Pat. No. 6,743,241 by Stephen Kerr, entitled, "Laparoscopic Port Site Fascial Closure Device." The stated device allows a surgeon to selectively deploy needles for positioning and stitching a suture across the puncture site that can ultimately be withdrawn from the puncture wound. Although the stated device has allowed for the deploying of a suture without the enlargement of the puncture site. The stated device also has associated disadvantages. In order to utilize the stated device the obturator and the cannula must be removed from the puncture site. This removal can cause temporary loss of the puncture site and/or some difficulty in the reinsertion of another cannula that is associated with the closing device. The removal of the first cannula also has time loss associated therewith.

Another disadvantage associated with the stated device is the inability to determine the extent of the penetration of the suturing needles into the peritoneum and fascia. Not knowing the penetration depth and the relation thereof to the thickness of the peritoneum and the fascia can result in a poor suture that may partially or fully open.

In addition, the stated device is use limited. The stated device is utilized solely for closure of a penetrated site and can only be used after there is no longer surgical use for the penetrated site and a decision is made to close the site.

Thus, there is a need for an improved laparoscopic technique and device for laparoscopic fascial closure that overcomes the above-stated disadvantages.

SUMMARY OF THE INVENTION

The present invention is an improved laparoscopic trocar and facial closure system. The invention includes a trocar having a shaft member and a pointed tip, a telescoping cannular assembly having a pair of sleeve members, a needle receptor assembly having another sleeve member that is positioned over the shaft member, a needle actuation mechanism with a needle actuation rod having a handle, a needle assembly, and a needle release mechanism. One of the sleeve members includes a body member, a C-shaped portion and a pair of wings. Also, a pivotal deployment mechanism can be utilized for deploying the wings.

DESCRIPTION OF THE PREFERRED EMBODIMENTS

DESCRIPTION OF THE INVENTION

A laparoscopic trocar and facial closure systems are herein provided. The closure systems may be used to perform the tasks that would normally be performed through the utilization of multiple laparoscopic tools. The closure systems may be used during a laparoscopic procedure to puncture into and through an internal organ, to place a cannula or port within the organ for insertion of cameras, lights, telescopes, or surgical instruments, and to suture the puncture site. The closure systems allow one to suture a puncture site without the enlargement of the associated punctured area.

The closure systems include various assemblies, mechanisms, and components, some of which are shown in FIGS. 1-10. FIGS. 1-10 are shown in relation to multiple system and method embodiments, which are described in detail below. Note that the assemblies, mechanisms, components, and methods are shown solely for example purposes are not meant to be all-inclusive. One skilled in the art would envision that the assemblies, mechanisms, components, and methods may be modified depending upon the application. Also, although the present invention is described primarily with respect to laparoscopic surgery associated with the abdomen of a patient, it may be applied to other surgical procedures and used in the surgery and closure of any hollow organ or viscus of human and animal anatomy.

Figure 1A:
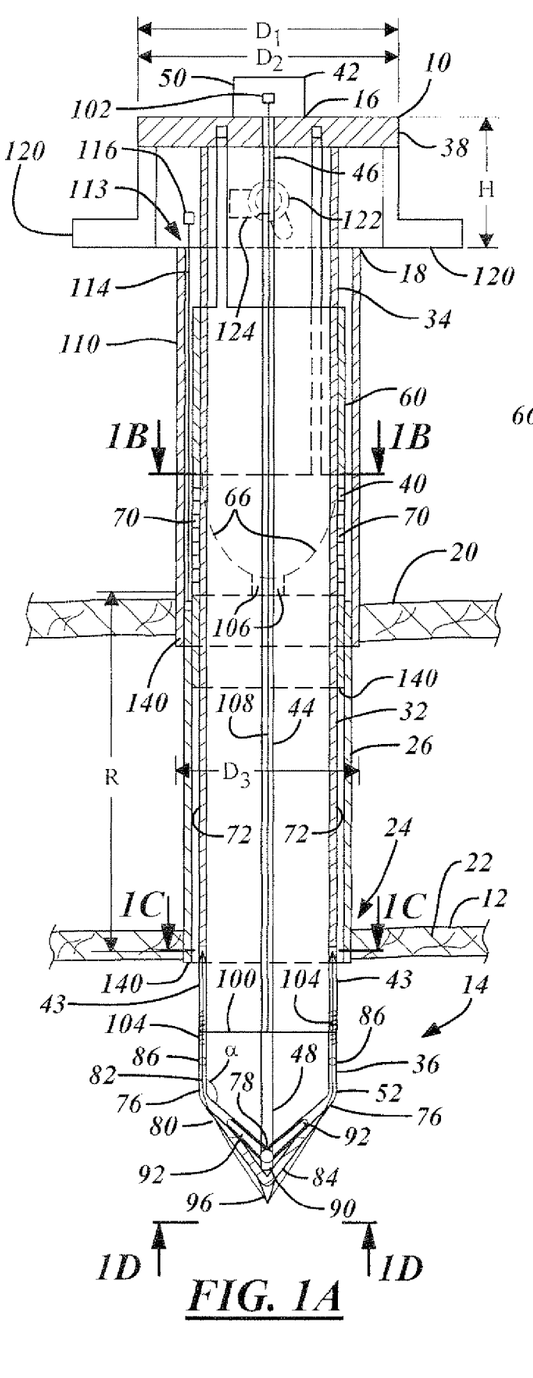
FIG. 1A depicts a first embodiment of the invention.
Figure 1B:
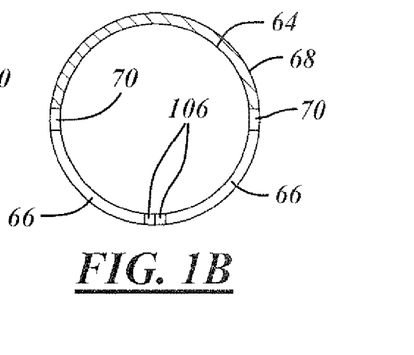
FIG. 1B and C are cross-sections of the embodiment shown in FIG. 1, with the cross-sections being taken along lines 1B-1B and 1C-1C, respectively, in FIG. 1.
Figure 1C:
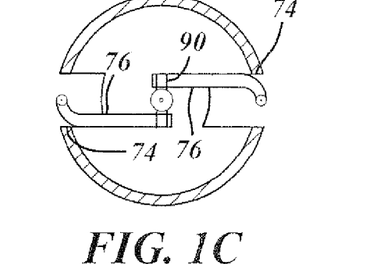

Referring to FIGS. 1A-C, a laparoscopic trocar and facial closure system 10 is shown in an initial undeployed state. In FIG. 1, a side cross-sectional view of the closure system 10 is shown upon insertion into a patient internal organ 12, such as an abdomen. The closure system 10, when appropriate, is inserted into the internal organ 12 after insufflation of the organ cavity 14. The closure system 10 includes a multipurpose trocar 16 that is inserted into a telescoping cannula assembly 18. The trocar 16, as with conventional trocars, is used to puncture the skin 20 of the patient and the organ wall 22. The trocar 16 is also used to close and suture the puncture site 24 of the organ wall 22. A lower cannula segment or port 26 of the cannula assembly 18 remains in the organ 12 during surgery and allows for the insertion of surgical equipment, such as cameras, telescopes, lights, and surgical tools.

The trocar 16 includes a main hollow shaft 32 that has an exposed end 34 and an unexposed end 36. The exposed end 34 is attached to a trocar housing 38. The trocar 16 also includes a needle receptor assembly 40 and a needle actuation mechanism 42. The needle receptor assembly 40 is attached to and/or slides over the shaft 32 and is used to receive and guide the needles 43. The needle actuation mechanism 42 includes a needle actuation rod 44 that is disposed through the center of the shaft 32. The rod 44 has a first end 46 and a second end 48. The first end 46 is coupled to a handle 50, which when stored rests on the trocar housing 38. The second end 48 is coupled to a needle assembly 52 on the unexposed end 36. Sliding translation of the rod 44 deploys and retracts the needle receptor assembly 40 and the needle actuation assembly 52.

Figures 4A, 4B, 4C, 4D:
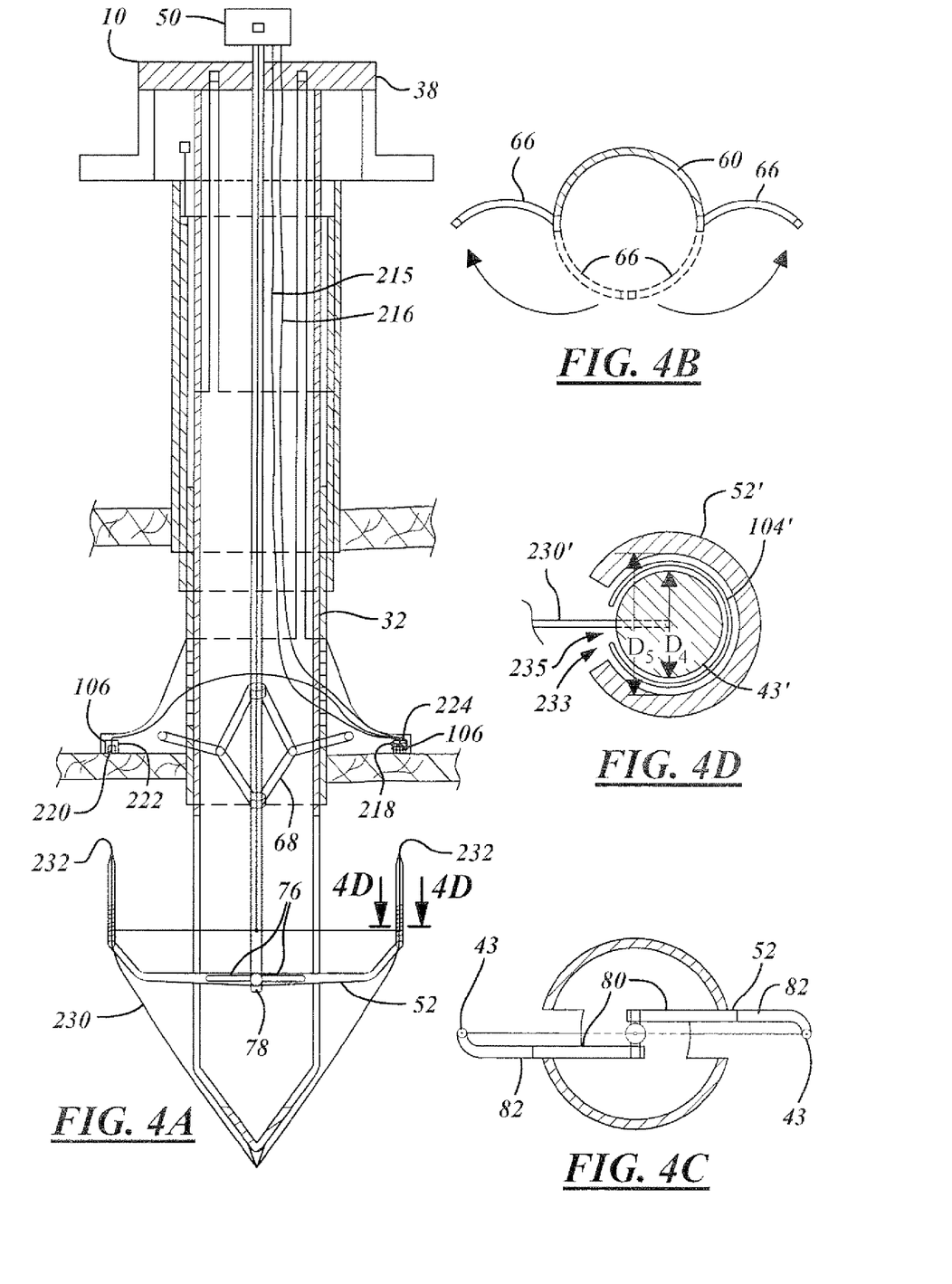
FIG. 4A illustrates a step in the deployment of an embodiment of the invention as shown in FIG. 1.
FIGS. 4B, 4C and 4D show cross-sectional views of the embodiment of the invention as shown in FIG. 4A.
Figure 5:
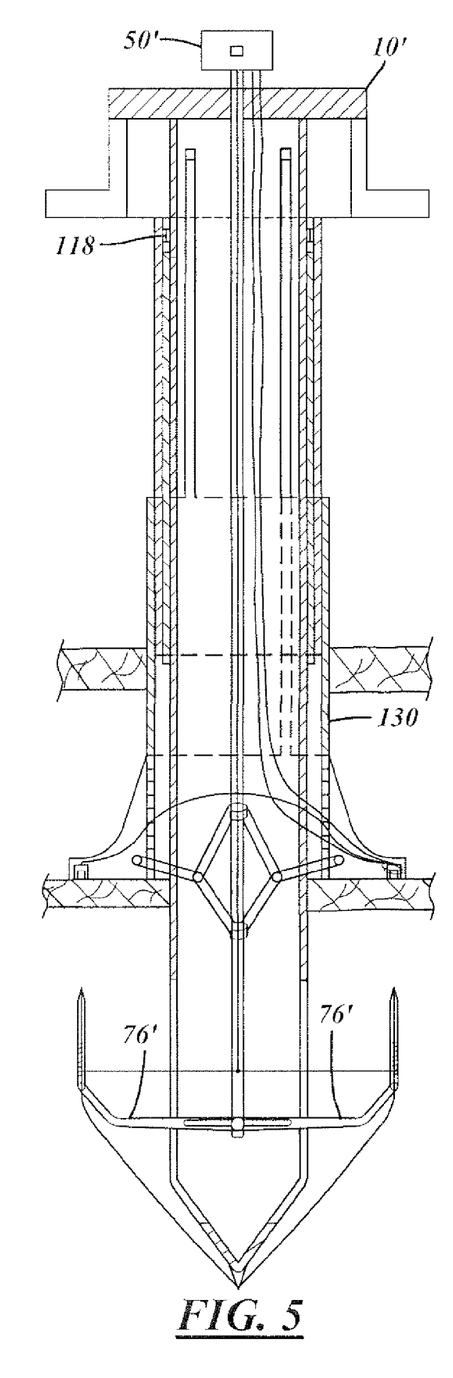
FIG. 5 illustrates another embodiment of the invention.
Figure 6:
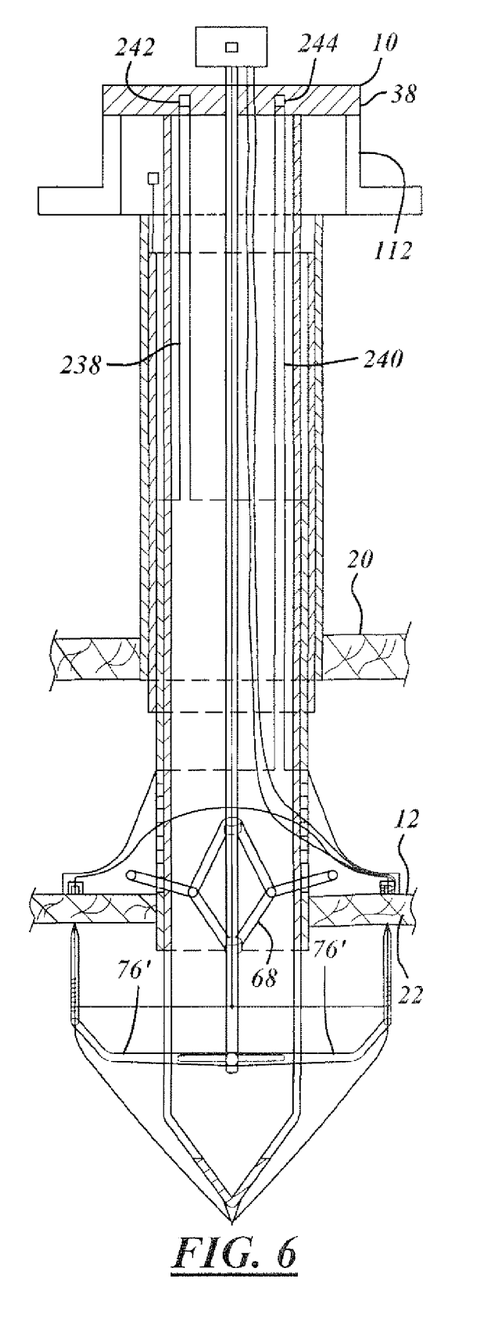
FIGS. 6 and 7 illustrates additional steps in the deployment of an embodiment of the invention as shown in FIG. 1.
Figure 7:
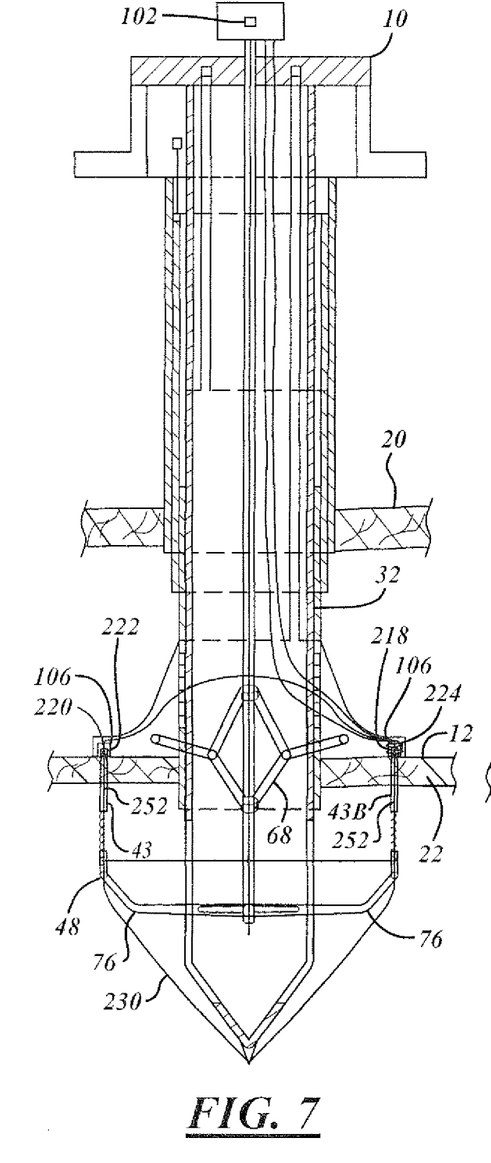

The needle receptor assembly 40, in the embodiment shown, includes a sleeve 60 that slides over the shaft 32. The sleeve 60 includes a body 62 having a 'C'-shaped portion 64 and a pair of wings 66. FIG. 1B shows a top cross-sectional view of the needle receptor assembly 40. The wings 66 are deployed via the handle 50. This deployment is shown in FIGS. 4a, 6, and 7. When the handle 50 is pulled away from the trocar housing 38 the linkages 68 within the shaft 32 are actuated, which causes the wings 66 (shown in phantom) to rotate laterally outward. The linkages convert the longitudinal translation of the rod 44 into rotational opening movement and deployment of the wings 66. The linkages 68 can best be seen in FIGS. 4a, 6, and 7. The wings 66 are attached to the body 62 via hinges/sliders 70. The wings 66 may be fixed to or slid longitudinally along the body 62 through use of the hinges/sliders 70. In another embodiment (not shown), the wings 66 and hinges/sliders 70 are coupled as part of and slide in the sidewalls 72 of the main shaft 32 and a sleeve, such as the sleeve 60 is not incorporated or utilized.

The needle assembly 52 includes two or more needles, such as the needles 43, which are used to suture the puncture site 24. FIG. 1C shows a top cross-sectional view of the needle assembly 52. In the embodiment shown and described herein two needles are used and shown. The needles 43 reside in slots or channels 74 on the sides 72. A pair of brackets 76 is coupled to the second end 36 via a pivot joint 78. Each of the brackets 76 has a tapered segment 80 and a needle-coupling segment 82. The angle $\alpha$ between the tapered segment 80 and the needle-coupling segment 82 is approximately 135°. The tapered segment 80 corresponds to a tapered tip portion 84 of the unexposed end 36. The needle-coupling segments 82 are attached to the needles 43 via needle hinges 86.

Figure 3:
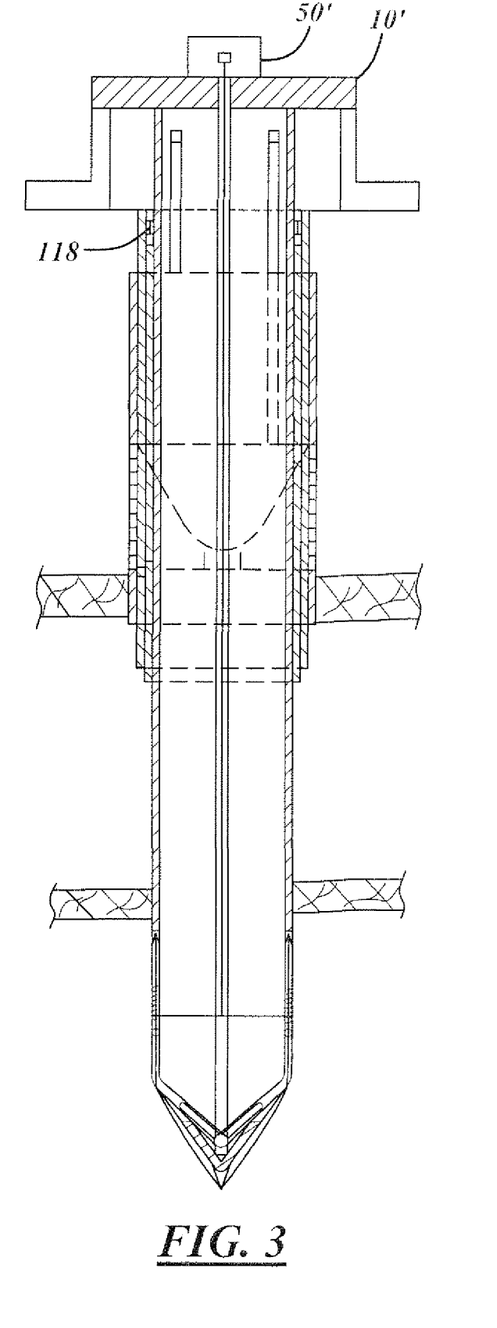
FIG. 3 illustrates an alternate embodiment of the invention.

When deployed, the rod 44 is pulled up by the handle 50, which causes the brackets 76 to slide on the pivot joint 78 or on one or more pegs 90 (only one is shown) thereof. The tapered segments 80 have slots 92 which allow the segments 80 to slide over the pegs 90. The movement of the brackets 76 separates the needles 43 from the shaft 32. This deployment is shown in FIGS. 4a, 6, and 7. Note that the needles 43 and the wings 66 are deployed simultaneously in one single displaced action of the rod 44. This is illustrated in FIG. 3. The brackets 76 rotate outward such that the needle-coupling segments 82 are approximately perpendicular to the organ wall 22.

The tip portion 84 cuts the tissue of the skin 84 and of the organ 12 to puncture therethrough. The tip portion may be constructed and shaped to provide the needed cutting. As an alternative or in combination thereof, the tip portion 84 may have a cutting element 96, as shown, such as a blade or some other cutting element attached thereto. The tip portion 84 may also have a protective shield (not shown), which is displaced to expose the cutting element 96. The protective shield may be used to prevent injury when handling the trocar 16.

The trocar 16 also includes a needle release mechanism 100. After deploying the needles 43 laterally outward away from the rod 44. The needles 43 are displaced and directed towards, into, and through the organ wall 22 via a needle trigger 102 located in the handle 50. The needles 43 are attached to springs 104, which are coupled to the needle hinges 86. When triggered, the springs 104 are released which causes the needles 43 to be projected toward the sockets 106 of the wings 66. The needle release mechanism 100 includes a wire 108 or some other line or mechanism that extends through the rod 44, as shown, or through the shaft 32 and is mechanically coupled to the springs 104 and/or the needles 43. When the trigger 102 is depressed the springs 104 expand pushing the needles through the organ wall. This action allows the needles 43 to penetrate the organ wall 22 without physical and manual displacement of the needles 43 by the surgeon. Notwithstanding, the trocar 16 may be manually lifted or pulled in an outward direction to direct the needles into and/or through the organ wall 22 as desired.

The cannula assembly 18 includes the port 26 and the tipper fixed segment 110. Although the cannula assembly is shown as having two segments, it may have any number of segments. The overall outer diameter $D_3$ of the port 26 and the fixed segment 110 may vary depending upon the application. In one example embodiment, the overall diameter $D_3$ is approximately 10 mm. The overall diameter $D_3$ may be less than or greater than 10 mm. The fixed segment 110 is rigidly attached to a cannula housing 112. The cannula assembly 18 includes a telescoping mechanism 113. The telescoping mechanism 113 may simply include the telescoping of the port 26 within the fixed segment 110 or may be more sophisticated. In another embodiment (not shown), the port segment 26 telescopes or slides over the fixed segment 110. The port 26 and the fixed segment 110 have overlapping portions (not shown) that prevent the port 26 from separating from the fixed segment 110. In one embodiment, as shown in FIGS. 1A, 4A, 6, and 7, the telescoping mechanism 113 includes a wire or spring 114 that extends from a telescoping control device 116 in the cannula housing 112 to the port 26. In another embodiment, as shown in FIGS. 2, 3, 5, and 8, the telescoping mechanism 113 includes a slider 118, which may be indirectly or directly attached to the port 26. The slider 118 is exposed through the fixed segment 110 and slides longitudinally in a channel (not shown) thereof.

The cannula housing 112 has an outer diameter $D_1$ that is approximately equal to the outer diameter $D_2$ of the trocar housing 38, such that the combination thereof provides a combined holding device. The trocar housing 38 and the cannula housing 112 may have finger grips to ease in the handling thereof, sample finger grips 120 are shown in FIG. 1A for the cannula housing 112. The finger grips may be integrally formed as part of the housings 38 and 112. The cannula housing 112 may have an insufflation/desufflation valve 122 with an air line adaptor 124. The height H of the cannula housing is approximately equal to or greater than 2 cm. The height H provides some increased flexibility in accommodating patients that have thick organ walls and/or thick fat cell layers surrounding the organ walls. The height H provides a surgeon with increased adjustment flexibility for the range R between the sockets 106 and the needles 43. The shaft 32 may be detached from the trocar housing 38 allowing shaft 32 to be inserted farther into the patient assuring that the needles 43 deploy within the organ 12 and the wings 66 deploy between the organ 12 and the skin 20.

Figure 2:
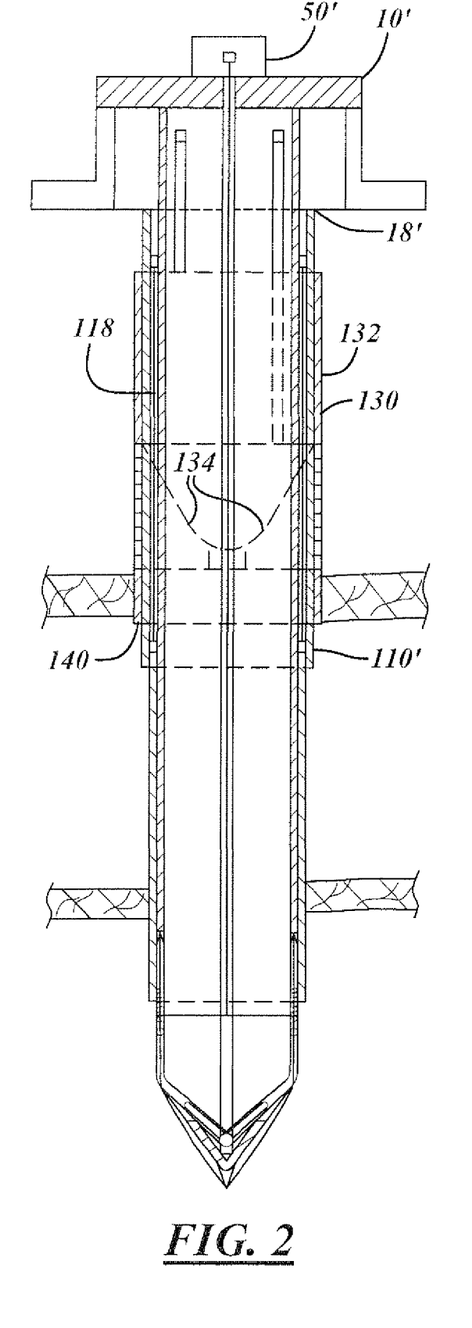
FIG. 2 illustrates an alternate embodiment of the invention.

In FIG. 2 another cannula assembly 18' of a laparoscopic trocar and facial closure system 10' is shown and includes a deployable needle receptor assembly 130 similar to the needle receptor assembly 60. The needle receptor assembly 130 is shown in stowed and deployed states in FIGS. 2, 3, 5, and 8. The needle receptor assembly 130 also includes a sleeve 132 and a pair of wings 134. The sleeve 132 is coupled to and slides over the fixed segment 110'.

Edges 140 of the sleeves 60 and 132 and of the segments 26 and 110 may be tapered to ease insertion thereof into the organ 12 and the skin 20.

The sutures should be positioned around the port during the operation.

Additional features and mechanisms of the closure systems are described in conjunction with the below described method. A method of performing a surgery including the facial closure techniques of a puncture site incorporating one or more of the closure systems described herein is described below in steps 200-276. The facial closure techniques include a suturing technique that is sometimes referred to as "Link Rail Roading," which is used to form a knot between two threads through the pulling of one of the threads.

In step 200, an internal organ of a patient may be insufflated using techniques known in the art. The organ may be insufflated prior or subsequent to the insertion of the closure systems. Prior insufflation expands the organ and provides increased volume in which to perform the surgery.

In step 202, the closure systems are inserted into the patient and through the wall of the organ. The cutting element and the configuration of the tip of each closure system are used to penetrate through the skin of the patient, the organ of concern, and any fat therebetween. The order of steps 202 and 200 may be interchanged. When the organ is insufflated after the insertion of the closure systems, an air line may be connected to the cannula housing of one or more of the closure systems via an adaptor, such as the adaptor 124. The associated air valve(s) are opened to permit gas, such as carbon dioxide, to fill and expand the organ.

Subsequent to step 202, step 204 is performed when the internal organ surgery is to be performed prior to placement of one or more suture threads. However, step 212 is performed when the internal organ surgery is performed subsequent to the placement of one or more suture threads.

The sutures should be positioned around the port during the operation.

In step 204, the trocars of the closure systems may be removed. The trocars are pulled out of the corresponding cannula assemblies. In step 206, the various lights, cameras, tools, and equipment need for the surgery are inserted into the cannula assemblies and the internal surgery on the organ is performed. In step 208, the various lights, cameras, tools, and equipment are removed from the cannula assemblies. In step 210, the trocars are reinserted into the cannula assemblies. Step 212 is performed subsequent to step 210.

In step 212, the deploying of one or more trocars is initiated. The port segments, of the selected trocars, are telescoped into or over the associated fixed segments.

In step 214, the needle receptor assembly wings and the suture needles of the selected trocars are deployed. The handles of the trocars, such as the handles 50 and 50', are pulled away from the trocar housings, thereby releasing the wings and the needle brackets. This stage is shown in FIGS. 4A-C and 5 for the closure systems 10 and 10'. FIGS. 4B and 4C show top cross-sectional views of the needle receptor assembly 60 and the needle assembly 52.

Figure 1D:
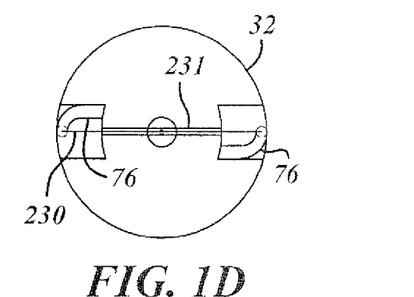
FIG. 1D is an end view of the embodiment shown in FIG. 1A.

Note that the active and passive suture threads 215 and 216 are shown between the handles and the trocar housings. In the embodiments shown in FIGS. 4a and 5-7 the active suture thread 215 extends down through the trocar housing 38, through the shaft 32 is coiled around a second thread receiver 224, which is in the first socket 218 and is attached to a first thread receiver 220 in the second socket 222. The active thread 215 is coiled such that it forms a clinch knot with the passive thread 216. The passive thread 216 extends down through the trocar housing 38, through the shaft 32, and attaches to the second thread receiver 224 in the first socket 218. A third thread or link 230 extends between the tips 232 of the needles 43. The link 230 extends within the needles 43, the brackets 76, and the groove 231 of the shaft 32. The groove 231 is best seen in FIG. 1D, which is a bottom view of the shaft 32. The suture threads 215 and 216 may be in the form of filaments that have cuff ends, similar to the receivers 220 and 224, for the reception and attachment to the tips of the needles 43.

In step 234, the trocars are pulled up such that the needles are in contact with the organ wall. In step 236, the sleeves and/or the wings of the needle receptor assemblies are pushed longitudinally inward along the shafts such that the wings abut the exterior surface of the organ wall. Of course, the closure systems are configured such that the needles remain in line with the sockets throughout the procedure. The sleeves and the wings may be manually pushed inward via a sleeve actuating mechanism and a wing actuating mechanism, such as the sleeve actuating mechanism 238 and the wing actuating mechanism 240 shown in FIGS. 1A, 2, 3, 4A, and 5-8. The sleeve actuating system 238 has a first trigger control 242 and the wing actuation system 240 has a second trigger actuation control 244. Each of the trigger controls 242 and 244 are located on the trocar housing 38.

In step 250, the needles, such as the needles 43, are released. The needle triggers, such as the needle trigger 102 and the like, are depressed and the associated springs are expanded driving the needles through the organ wall and into the sockets, such as the sockets 106. The sockets also limit the displacement of the needles. The needle release mechanism in combination with the sockets assures accurate displacement of the needles without visual sight thereof. In so doing, the ends of the third threads or links are attached to the thread receivers. For example, the thread ends 252 are attached to the thread receivers 220 and 224. This connection of the third threads connects the active threads to the passive threads to form single continuous thread lines in each closure system. This stage is shown in FIG. 7.

Figure 8:
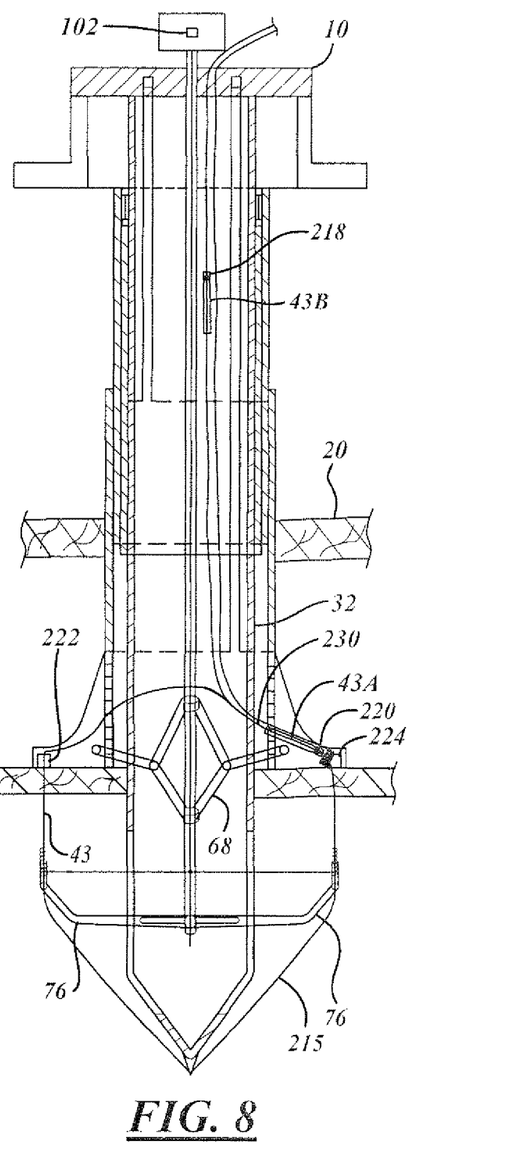
FIGS. 8-10 illustrate steps in the use of an embodiment of the invention.

In step 254, the active threads are pulled causing the links, needles, and thread receivers to be pulled through the brackets and into the shafts. FIG. 4D illustrates an example relationship between a link 230', a bracket 52', a needle 43', and a spring 104'. FIG. 4D is an example top view of a deployed bracket as a needle is being pulled therethrough. Notice that the outer diameter $D_4$ of the needle 43' is less than the inner diameter $D_5$ of the bracket 52'. The link 230' may be pulled out of the bracket 52' and the spring 104' through the open side portions 233 and 235, respectfully, thereof. The bracket 52' and the spring 104' are 'C'-shaped near the portions 233 and 235 to allow removal of the link 230'. For example, the first thread receiver 220 and the corresponding needle are pulled out of the second socket 222, through the brackets 76, through the groove 231 and/or around the exterior of the tapered tip portion 84, and into the shaft 32. This is shown in FIG. 8.

Figure 9:
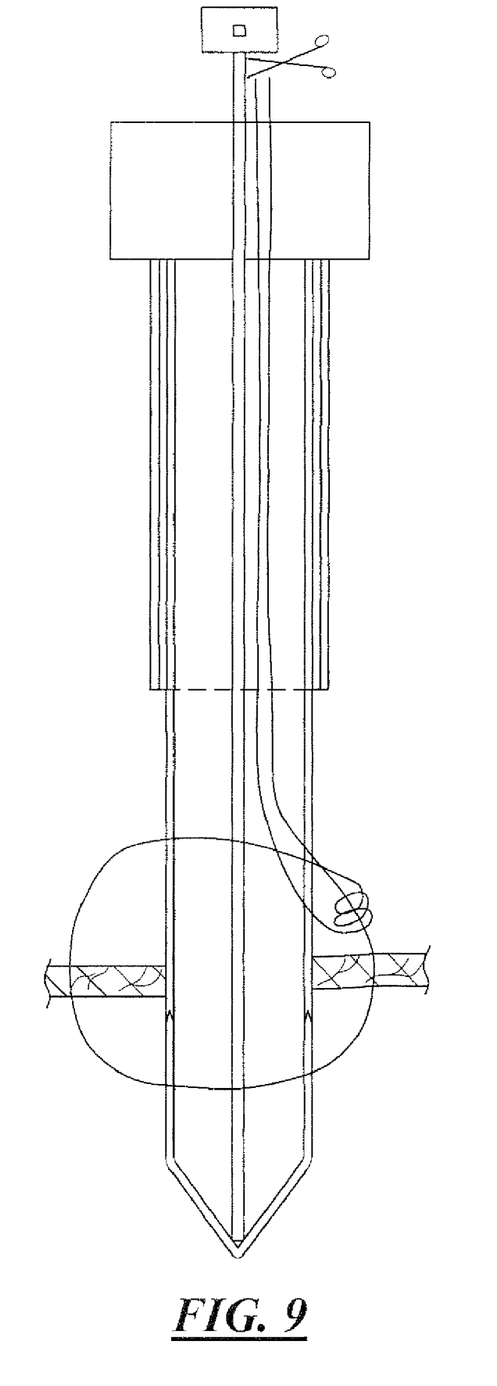
Figure 10:
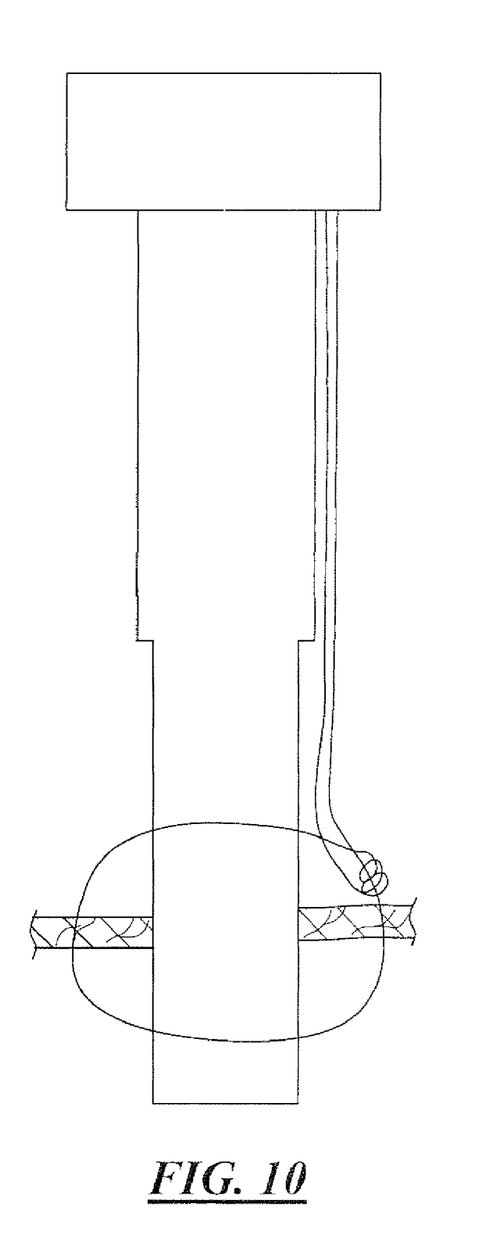

In step 256, the needle receptor assemblies and the needles are stowed, or in other words, closed and returned into the shafts of the trocars. In step 258, the ports are reinserted into the organ. In step 260, the trocars are removed from the cannula assemblies, while at the same time leaving the continuous thread lines within the patient and organ, with the ends thereof extending out of the patient skin. The trocars are pulled out and over the portions of the continuous thread lines that are exterior to the organ. This is shown in FIGS. 9 and 10.

Subsequent to step 260, step 262 is performed when the suture threads are placed after internal organ surgery. Step 268 is performed when the suture threads are placed before internal organ surgery.

In step 262, the organ is desufflated. In step 264, the cannula assemblies are removed from the patient. In step 266, the continuous threads are pulled to close and suture the penetrated sites in the organ.

In step 268, the various lights, cameras, tools, and equipment need for the surgery are inserted into the cannula assemblies and the internal surgery on the organ is performed. In step 270, the various lights, cameras, tools, and equipment are removed from the cannula assemblies. In step 272, the organ is desufflated. In step 274, the cannula assemblies are removed from the patient. In step 276, the continuous thread lines are pulled to close and suture the penetrated sites in the organ, as performed in step 266.

What is claimed is:

1. A laparoscopic trocar and facial closure system comprising:
    a trocar having a shaft member and a pointed tip;
    a needle receptor assembly comprising a sleeve member that is positioned over said shaft member, said sleeve member including a body portion having a C-Shaped portion and a pair of wings, said pair of wings in communication with a plurality of linkages within said shaft member and movable between a wing stored position and a wing deployed position, first and second sockets positioned on one of said pair of wings respectively;
    a suture thread passing down said shaft member, said suture thread coiled around said first socket and affixed to said second socket;
    a passive thread passing down said shaft member and affixed to said first socket;
    a needle actuation mechanism comprising a needle actuation rod, said rod having a handle, said needle actuation rod in communication with said linkages such that said handle is configured to move said pair of wings from said wing stored position to said wing deployed position;
    a needle assembly attached to said needle actuation rod opposite said handle, said needle assembly movable between a needle stored position and a needle deployed position, said needle actuation rod configured to move said needle assembly from said needle stored position to said needle deployed position as said wings are moved from said wing stored position to said wing deployed position, said needle assembly configured to deploy on an interior side of an organ wall and said pair of wings configured to deploy on an exterior side of the organ wall, said needle assembly including first and second needles joined together by way of a link element;
    a needle trigger configured to drive said first and second needles through the organ wall when activated in said wing deployed position and said needle deployed position, said first needle configured to lock into said first socket and said second needle configured to lock onto said second socket;
    wherein said passive thread is configured to pull said first socket such that said first and second sockets along with said needle assembly are pulled through said coiled portion and said end portion is pulled downward through the organ wall and back upwards through the organ wall and said coiled portion to form a suture within the organ wall and automatically creating a suture knot.

2. A laparoscopic trocar and facial closure system as described in claim 1 further comprising pivotal deployment mechanism for deploying said pair of wings.

3. A laparoscopic trocar and facial closure system as described in claim 1 wherein said suture knot is formed by pulling said suture thread downward into the organ wall, across the organ wall opening, and back up through the organ wall and the suture thread coil.

4. A laparoscopic trocar and facial closure system as described in claim 1 wherein said link element comprises a thread element extending within said first and second needles.

* * * * *